United States Patent
Schubert (10) Patent No.: US 12,076,476 B2
(45) Date of Patent: *Sep. 3, 2024

(54) HLM PUMP STOP REACTION

(71) Applicant: LivaNova Deutschland GmbH, Munich (DE)

(72) Inventor: Friedemann Schubert, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/209,129

(22) Filed: Jun. 13, 2023

(65) Prior Publication Data

US 2023/0321333 A1    Oct. 12, 2023

Related U.S. Application Data

(63) Continuation of application No. 17/393,161, filed on Aug. 3, 2021, now Pat. No. 11,690,943, which is a
(Continued)

(51) Int. Cl.
*G05B 23/02*      (2006.01)
*A61M 1/36*       (2006.01)
(Continued)

(52) U.S. Cl.
CPC ........ *A61M 1/3666* (2013.01); *A61M 1/3607* (2014.02); *G08B 5/22* (2013.01);
(Continued)

(58) Field of Classification Search
USPC ......... 340/679, 672, 691.1, 690, 691.6, 692, 340/693.2, 3.43, 825.23, 815.48, 330,
(Continued)

(56) References Cited

U.S. PATENT DOCUMENTS

| | | | | |
|---|---|---|---|---|
| 4,949,823 | A | * 8/1990 | Coutant | B62D 11/183 192/221 |
| 11,690,943 | B2 | * 7/2023 | Schubert | G08B 21/18 340/679 |
| 2003/0218623 | A1 | * 11/2003 | Krensky | A61M 1/159 604/29 |

(Continued)

FOREIGN PATENT DOCUMENTS

| | | |
|---|---|---|
| EP | 3050584 A1 | 8/2016 |
| JP | H06121832 A | 5/1994 |
| JP | 3240167 B2 | 12/2001 |
| WO | 9808564 A1 | 3/1998 |

OTHER PUBLICATIONS

International Search Report and Written Opinion, dated Nov. 25, 2019, for International Application No. PCT/EP2019/054664.

*Primary Examiner* — Daniel Previl
(74) *Attorney, Agent, or Firm* — Seager, Tufte & Wickhem LLP (57) ABSTRACT

A heart lung machine (HLM) includes: a pump actuator; an actuator control unit (ACU) operably connected to the pump actuator; a processing unit configured to receive a set of parameter data from the actuator; a display device configured to present a subset of the set of parameter data; and an input control device operably connected to the pump actuator. The input control device includes a rotatable knob. The ACU may be configured to: determine that the pump actuator has been stopped in response to a pump-stop trigger event; determine that the rotatable knob has been rotated to a first position; and in response to determining that the rotatable knob has been rotated to the first position, starting the pump actuator.

16 Claims, 8 Drawing Sheets

Related U.S. Application Data continuation of application No. PCT/EP2019/054664, filed on Feb. 26, 2019.

(51) Int. Cl.
*G08B 5/22* (2006.01)
*G08B 21/18* (2006.01)

(52) U.S. Cl.
CPC ......... *G08B 21/18* (2013.01); *A61M 2205/18* (2013.01); *A61M 2205/3334* (2013.01); *A61M 2205/502* (2013.01)

(58) Field of Classification Search
USPC ........................................ 340/5.73
See application file for complete search history.

(56) References Cited

U.S. PATENT DOCUMENTS

| | | | |
|---|---|---|---|
| 2007/0080174 A1* | 4/2007 | Coe | B05B 11/1059 222/153.13 |
| 2007/0199439 A1* | 8/2007 | Stephens | E02F 9/2004 91/525 |
| 2010/0329892 A1* | 12/2010 | Brantley | F04B 17/05 417/375 |
| 2011/0295177 A1* | 12/2011 | Mohl | A61M 1/3613 604/509 |
| 2015/0238674 A1* | 8/2015 | Hatanaka | A61M 1/3666 422/45 |
| 2017/0294146 A1 | 10/2017 | Grubbs | |
| 2019/0099542 A1 | 4/2019 | Kuzelka | |
| 2019/0388598 A1 | 12/2019 | Ratner et al. | |
| 2021/0106809 A1 | 4/2021 | Solem | |

* cited by examiner

HLM PUMP STOP REACTION

CROSS REFERENCE TO RELATED APPLICATIONS

This application is a continuation of U.S. patent application Ser. No. 17/393,161, filed on Aug. 3, 2021, which is a continuation of International Application No. PCT/EP2019/054664, filed Feb. 26, 2019, the disclosures of which are incorporated herein by reference.

TECHNICAL FIELD

The present disclosure relates to medical equipment, in particular, fluid pump systems for heart lung machines.

BACKGROUND

Heart lung machines include fluid pumps that sometimes are stopped as a result of pump-stop trigger events such as errors or alarms (e.g., a bubble alarm). In many HLMs, upon an occurrence of a pump stop, the user must perform one of a number of actions in order to start the pump again, which may require the user to take his or her hand off of the control knob used to control the speed of the pump. For example, the user may be required to override an alarm on a system display device, delete an alarm on a system display device, press a global override button on the pump, switch off a sensor, and/or the like.

SUMMARY

Embodiments include a heart lung machine (HLM), that includes: a pump actuator; an actuator control unit (ACU) operably connected to the pump actuator; a processing unit configured to receive a set of parameter data from the actuator; a display device configured to present a subset of the set of parameter data; and an input control device operably connected to the pump actuator. In embodiments, the input control device includes a rotatable knob. The ACU may be configured to: determine that the pump actuator has been stopped in response to a pump-stop trigger event; determine that the rotatable knob has been rotated to a first position; and in response to determining that the rotatable knob has been rotated to the first position, starting the pump actuator.

Embodiments include a method of operating a heart lung machine (HLM), the HLM including a pump actuator, an actuator control unit (ACU) operably connected to the pump actuator, a processing unit configured to receive a set of parameter data from the actuator, a display device configured to present a subset of the parameter data, and an input control device operably connected to the pump actuator. The input control device may include a rotatable knob. In embodiments, the method includes: detecting an occurrence of a pump-stop trigger event; stopping operation of the pump actuator; determining that the rotatable knob has been rotated to a first position; and starting the pump actuator in response to determining that the rotatable knob has been rotated to the first position.

Embodiments include a blood pump system for use with a heart lung machine (HLM). The system may include a pump actuator; an actuator control unit (ACU) operably connected to the pump actuator; and an input control device operably connected to the pump actuator. The input control device may include a rotatable knob. The ACU may be configured to: determine that the pump actuator has been stopped in response to a pump-stop trigger event; determine that the rotatable knob has been rotated to a first position; and in response to determining that the rotatable knob has been rotated to the first position, starting the pump actuator.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Figure 1A:
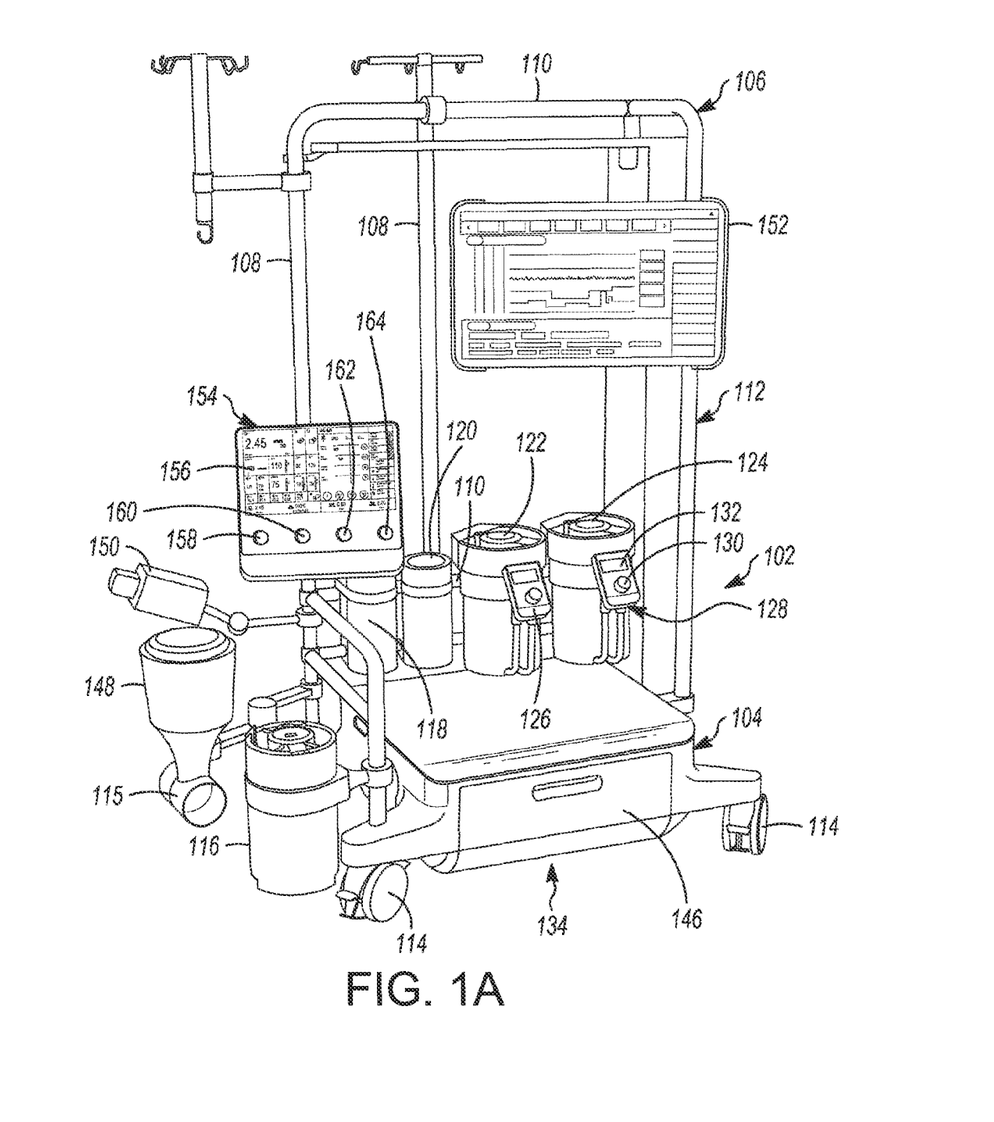
FIG. 1A is a front perspective view of an illustrative heart lung machine (HLM), in accordance with embodiments of the subject matter disclosed herein.
Figure 1B:
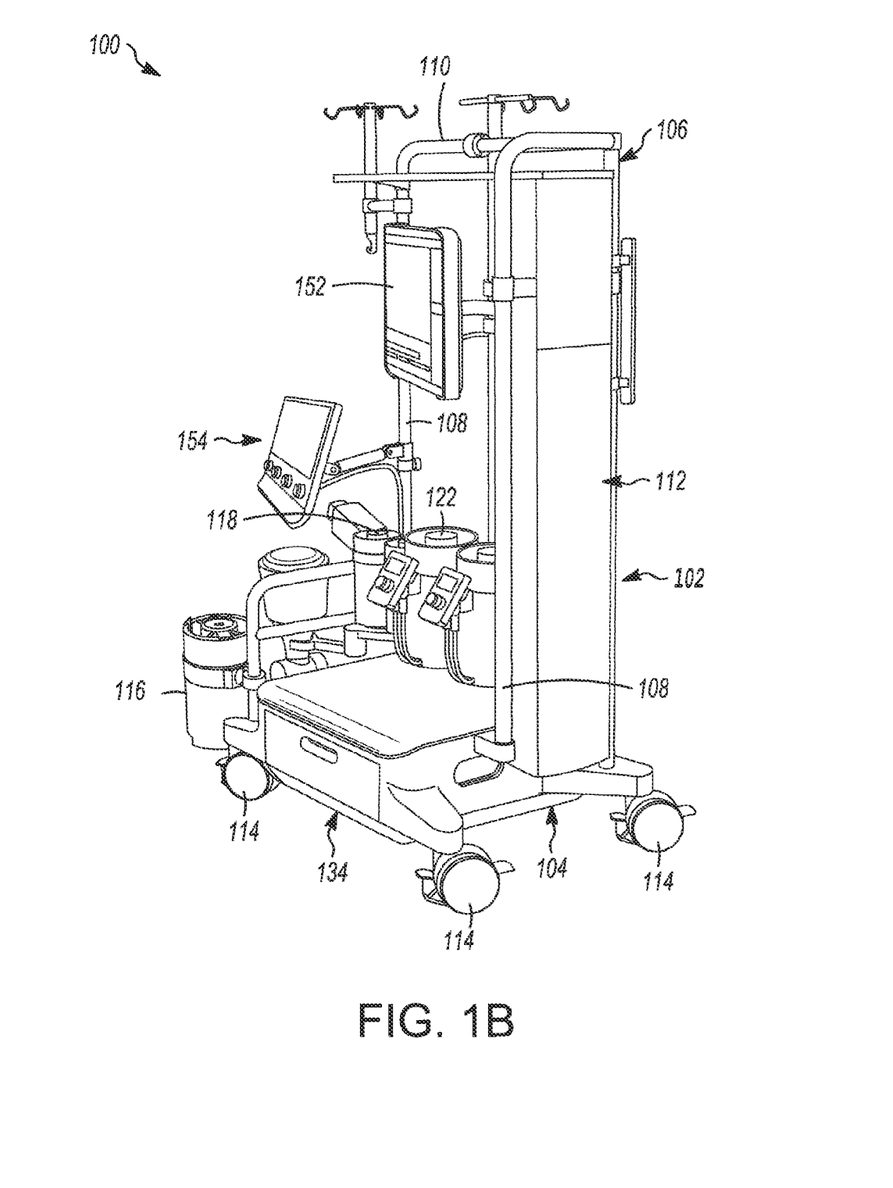
FIG. 1B is a side perspective view of the illustrative HLM depicted in FIG. 1A, in accordance with embodiments of the subject matter disclosed herein.

FIG. 1A is a front perspective view of an illustrative heart lung machine (HLM) 100, in accordance with embodiments of the subject matter disclosed herein; and FIG. 1B is a side perspective view of the illustrative HLM 100 depicted in FIG. 1A, in accordance with embodiments of the subject matter disclosed herein. As shown, the HLM 100 includes a trolley 102 having a base 104 that includes an internal cavity (not shown) for housing any number of different controls, electrical circuits, hydraulic circuits, a battery discharger, and/or the like. For example, in embodiments, a peripheral processing unit may be disposed within the base 104. A mast assembly 106 is coupled to the base 104 and extends upwards from the base 104. The mast assembly 106 may include any number of different mast components, including vertical poles 108, horizontal rails 110, and/or the like. In embodiments, the trolley 102 includes an enclosure 112 that is configured to facilitate cable management, provide A/C outlets, include a power switch for the HLM 100, include an extension box, and/or the like. As shown, the trolley 102 also may include wheels 114 coupled to the base 104.

As shown, the HLM 100 also may include a number of different types of components such as an oxygenator 115 (which may actually be considered to be an element of an extracorporeal circuit used with the HLM, but may be referred to herein as being a component of the HLM due to being connected to the trolley 102); pumps 116, 118, 120, 122, 124; and/or the like. In embodiments, one or more of the components 115, 116, 118, 120, 122, and 124 (and/or others) may be coupled to any number of different portions of the mast assembly 106, and may include, for example, an exposed actuator control unit (ACU). For example, as shown, pumps 122 and 124 may each include an exposed ACU 126 and 128, operably connected thereto, respectively. As shown, an ACU 128 may include a control knob 130 configured to receive user input (e.g., manipulation of the knob 130) for controlling operation of the pump 124, and an information display device 132 configured to present information associated with the pump such as, for example, one or more parameters (e.g., measured device parameters such as, for instance, flow, rpm, etc.). According to embodiments, an ACU may be configured to facilitate control of a pump, a motorized clamp, a motorized occluder, an infusion device, and/or any number of other types of devices that may be associated with an HLM.

Traditionally, HLMs have utilized roller pumps that are each integrated into a modular console component. The modular console components are stacked next to one another on the base of an HLM to provide an array of pumps. The modular console component also houses an ACU having an interface for controlling the corresponding integrated roller pump. One advantage of having the ACU interface provided at the modular console component is that, during an emergency situation, the perfusionist can easily determine the ACU that corresponds to a particular roller pump. More recently, mast mounted roller pumps (without the modular console component housing) have been utilized in HLMs. Mast mounted pumps provide more flexibility in the configuration of the HLM; however, if the ACUs for the mast mounted pumps are located remotely, or detached from, the mast mounted pumps, it's potentially more difficult for the perfusionist to identify the ACU that controls a particular pump.

Embodiments of the present disclosure include mast mounted roller pumps, such as pumps 122 and 124 of FIG. 1A, having corresponding ACUs, such as ACUs 126 and 128, respectively. The ACUs 126 and 128 are attached, connected, or otherwise operatively coupled to the corresponding mast mounted roller pumps 122 and 124. The connectedness, or close proximity of the ACU to the mast mounted roller pump allows the user to precisely determine the ACU that controls a particular mast mounted roller pump in a high pressure, or emergency situation, including a situation where the control display device 156 is not functioning properly or is disabled. Thus, the ability to mount the pumps 122 and 124 to the mast assembly 106 allows a much wider range of configurations to meet the user's particular needs.

Figure 1C:
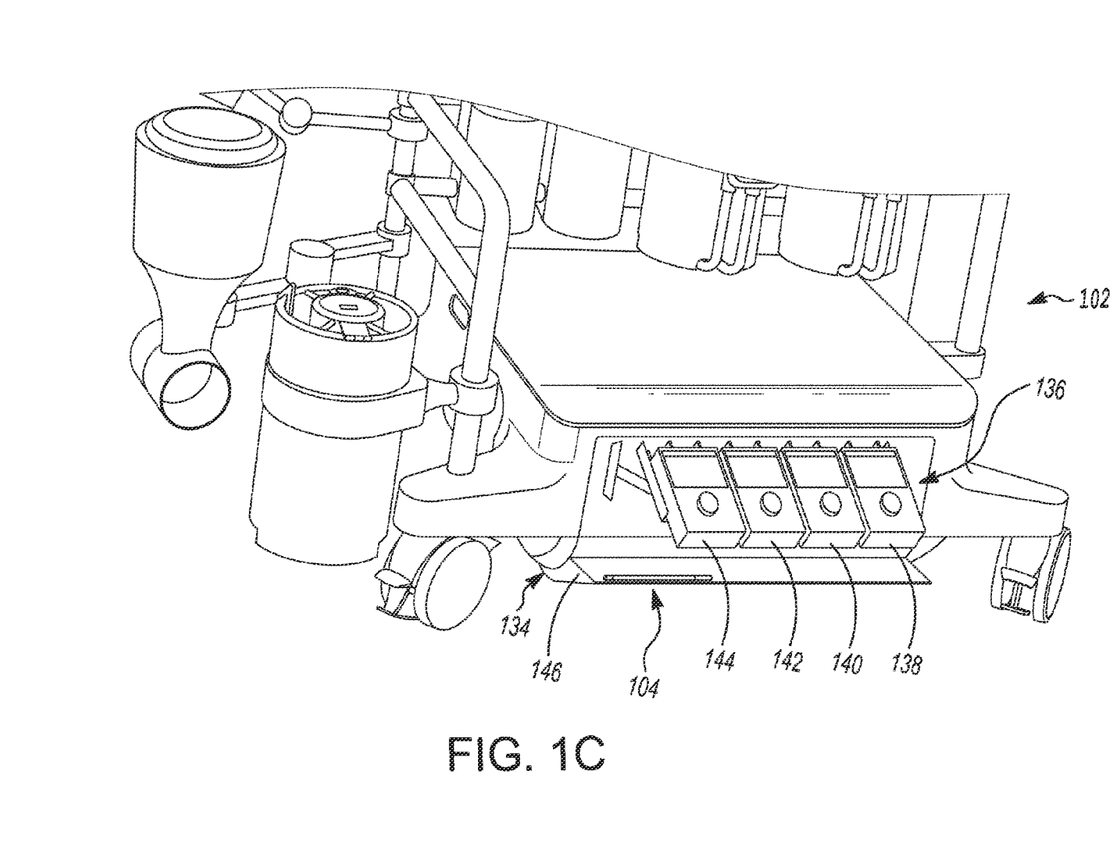
FIG. 1C is a partial perspective view of the base of the trolley depicted in FIGS. 1A and 1B, in accordance with embodiments of the subject matter disclosed herein.

FIG. 1C is a partial perspective view of the base 104 of the trolley 102 depicted in FIGS. 1A and 1B, in accordance with embodiments of the subject matter disclosed herein. As shown in FIG. 1C, the base 104 of the trolley 102 may include a lower housing 134 having an enclosure 136 configured to house one or more ACUs 138, 140, 142, and 144. In embodiments, any number of ACUs may be disposed in the enclosure 136. For example, in embodiments, all of the ACUs for actuators associated with the HLM 100 may be disposed at least partly in the enclosure 136. In embodiments, one or more ACUs may be exposed by being disposed directly on or near the corresponding actuators. According to embodiments, the enclosure 136 may be configured to be closed to protect the ACUs disposed therein, or opened to reveal the ACUs. For example, the lower housing 134 may include a drawer, cabinet, and/or the like. As shown, in embodiments, the lower housing 134 may include a door 146 configured to be opened and closed to selectively expose or conceal the enclosure 136. Each of the ACUs 138, 140, 142, and 144 may be operably connected to a corresponding one of the components 116, 118, 120, 122 (e.g., in cases in which the pump 122 does not include an exposed ACU 126), or 124 (e.g., in cases in which the pump 124 does not include an exposed ACU 128) and/or other actuators.

As is further shown in FIGS. 1A and 1B, the HLM 100 may include any number of other components such as, for example, a venous reservoir 148 (which may be, for example, a component of an extracorporeal circuit that may be used in combination with the HLM 100), an electronic venous occluder (EVO) 150, a peripheral display device 152, a control assembly 154, any number of various types of sensors, and/or the like. According to embodiments, any number of the components discussed herein, others not discussed herein, or aspects of the components (e.g., sensors and/or actuators associated with components) may be operably connected to the peripheral processing unit (not shown), which may be configured to receive parameter data from any one or more of the components, process parameter data, receive control signals from any one or more input devices (e.g., ACU control knobs 130, etc.), provide control signals to any one or more of the components, and/or the like.

In embodiments, the peripheral display device 152 may be operably connected to the peripheral processing unit and configured to present a set of parameter data received from the peripheral processing unit. In embodiments, the peripheral display device 152 may be, include, or be included within a data recording and/or management system. That is, for example, the peripheral display device 152 may include, or be otherwise associated with, a processing unit separate from that of the HLM, and/or may be configured to record and/or display any number of different operative HLM parameters. In some implementations, for example, the peripheral display device 152 may be configured to obtain and record all of the operative HLM parameter values and/or patient parameters provided by any number of additional monitoring devices. The peripheral display device 152 may be configured to present, graphically, representations of any number of the obtained parameter values, changes in parameter values over time, derived parameter values (e.g., values derived from parameter values), and/or the like.

During an operation, the primary focus of a user of the HLM 100 generally is the oxygenator 115 and the venous reservoir 148. Accordingly, embodiments of the subject matter disclosed herein provide a control assembly 154 near those two components 115 and 148 so that the user can access control devices and view displayed parameters without having to move away from, or be distracted from, the oxygenator 115 and venous reservoir 148. According to embodiments, the control assembly 154 may include a control display device 156 and a number of input control devices 158, 160, 162, and 164. In embodiments, the control assembly 154 may include any number of input control devices (e.g., 1, 2, 3, 4, 5, 6, etc.) and the number of input control devices may be less than or equal to the number of ACUs in the enclosure 136. The control display device 156 may be configured to present a subset of the parameters presented by the peripheral display device 152 and/or the peripheral display device 152 may be configured to present a subset of the subset of parameters presented by the control display device 156. A different subset of the set of parameter data may be displayed by the peripheral display device 152. In embodiments, the peripheral display device 152 may be configured to display real-time waveform traces, while the control display device 156 may be configured to display numerical representations of the same and/or different parameters.

That is, for example, regardless of what is displayed on the peripheral display device 152, the control display device 156 may be configured to display a specified subset of parameter data that is particularly useful and/or important with respect to a procedure being performed. That specified subset of parameter data may be predetermined, based on the type of procedure; dynamically presented, based on a status of the patient and/or device; and/or the like. In embodiments, all of the information configured to be presented on the control display device 156 may be presented simultaneously—that is, without having tabs for accessing screens showing additional information, without requiring menus for accessing screens showing additional information during a procedure, and/or the like. In embodiments, the control display device 156 may include selectable representations presented onscreen that can be used to configure the display such as, for example, by enabling a user to select a display mode corresponding to a particular HLM component (e.g., a centrifugal pump, a roller pump, etc.), to select a particular display module (e.g., a pre-configured set of data fields in a particular arrangement), and/or the like.

According to embodiments, the peripheral display device 152 and/or the control display device 156 may include an input mechanism configured to enable user interaction with one or more features displayed on the display device 152 and/or 156. That is, for example, the peripheral display device 152 and/or the control display device 156 may be, or include, a touchscreen device configured to receive user input. In embodiments, the peripheral display device 152 and/or the control display device 156 may include an input device connected thereto such as, for example, a mouse, a trackpad, a joystick, and/or the like.

According to embodiments, for example, additional data from devices external to the HLM (e.g., blood gas monitors, electrocardiographs, ventilators, patient monitors, etc.) may be displayed on the peripheral display device 152. As indicated above, the peripheral display device 152 may be controlled by a peripheral processing unit that is separate from the central system unit, the control display device or any other central unit of the HLM. The peripheral processing unit associated with the peripheral display device 152 may be configured to obtain parameter values (e.g., from the central system unit, sensors, actuators, external devices, etc.) and may be configured to collect the data in a database. The peripheral processing unit may be communicatively coupled to the peripheral display device 152, HLM components, and/or external devices. In embodiments, while the peripheral processing unit may be configured to receive data from the central system unit, an interface unit or any other communication port embedded in the HLM, the peripheral processing unit may be configured so as to not send any data to the central system unit, to the interface unit or other communication ports of the HLM. In other embodiments, the peripheral processing unit and the central system unit, the interface unit or any other communication port of the HLM may be configured to exchange data with one another and/or other devices. According to embodiments, a user may select which data is to be stored by which processing or system unit.

The peripheral processing unit associated with the peripheral display device may be configured to allow user interaction therewith, generate reports based on the obtained data, generate printable documents corresponding to a medical procedure, interact with a printer to cause the printer to print such reports, and/or the like. In embodiments, the peripheral processing unit may be configured to generate, and cause the peripheral display device to present, graphs (e.g., trend charts, curves, etc.) and/or other visual representations of any number of various aspects of data received from HLM components and/or external devices. In embodiments the peripheral display device may be configurable such that a user can select certain types of data and/or representations thereof to display, the manner in which it is displayed, and/or the like. In contrast, for example, the control display device 156 may include only limited configurability, if at all. In this manner, the control display device 156 can be relied upon to present representations of data relevant to the HLM's current use. According to other embodiments, the control display device 156 may have any amount of configurability.

In embodiments, each of the input control devices 158, 160, 162, and 164 may be operably connected to one of the actuators and may be configured to receive user input for controlling an operation of the actuator. According to embodiments, the input control devices 158, 160, 162, and 164 may be operably connected to the respective ACUs 138, 140, 142, and 144, in which case, the input control devices 158, 160, 162, and 164 act in parallel to the ACUs, but do not have priority over them in controlling the actuators. In embodiments, the input control devices are directly connected to the respective ACUs, and the ACUs are connected to the respective actuators, such that an actuator can be controlled by an input control device only through an ACU or directly by an ACU. Therefore, the ACU has prevalence over the input control device in controlling the actuator.

The illustrative HLM 100 shown in FIGS. 1A-1C is not intended to suggest any limitation as to the scope of use or functionality of embodiments of the present disclosure. The illustrative HLM 100 also should not be interpreted as having any dependency or requirement related to any single component or combination of components illustrated therein. Additionally, various components depicted in FIGS. 1A-1C may be, in embodiments, integrated with various ones of the other components depicted therein (and/or components not illustrated), all of which are considered to be within the ambit of the present disclosure.

Figure 2A:
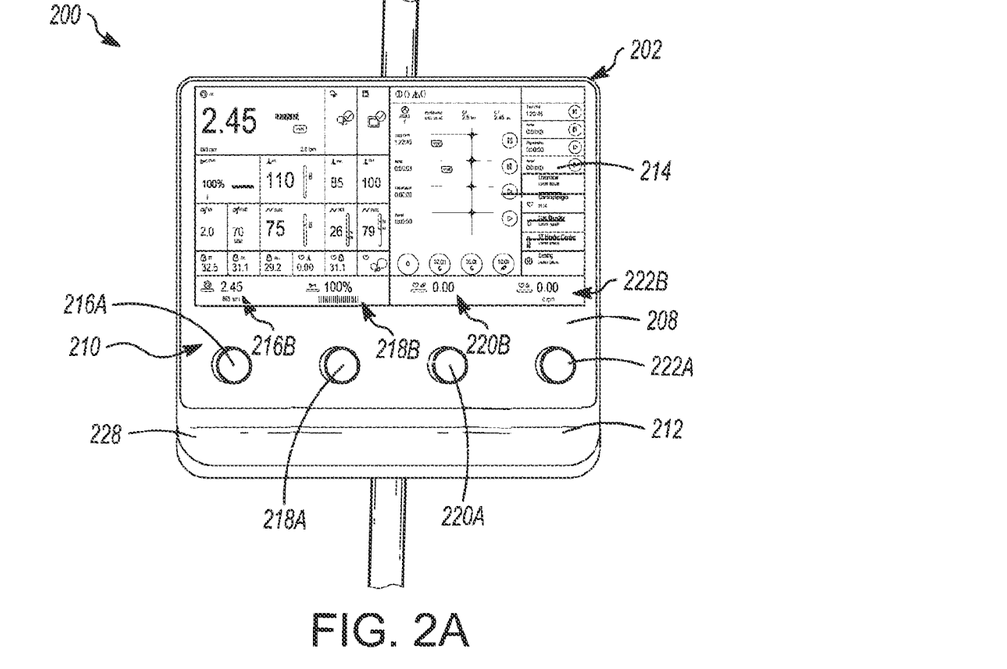
FIG. 2A is a front perspective view of an illustrative control assembly, in accordance with embodiments of the subject matter disclosed herein.
Figure 2B:
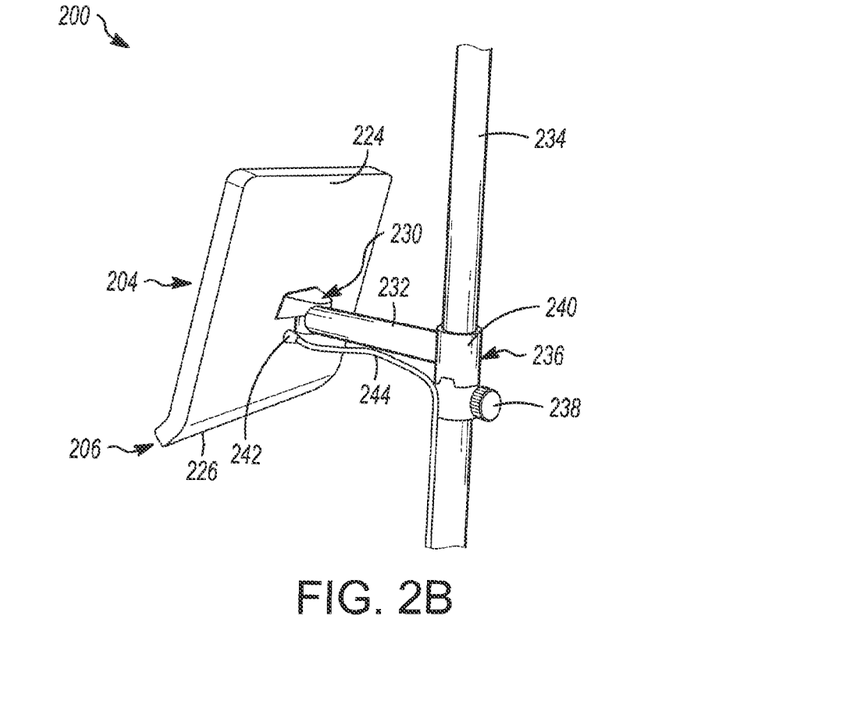
FIG. 2B is a rear perspective view of the illustrative control assembly depicted in FIG. 2A, in accordance with embodiments of the subject matter disclosed herein.

FIG. 2A is a front perspective view of an illustrative control assembly 200 of an HLM, in accordance with embodiments of the subject matter disclosed herein; and FIG. 2B is a rear perspective view of the illustrative control assembly 200 depicted in FIG. 2A, in accordance with embodiments of the subject matter disclosed herein. According to embodiments, the illustrative control assembly 200 may be, be similar to, include, or be included within the control assembly 154 depicted in FIGS. 1A-1B. In embodiments, the control assembly 200 may be configured to provide a graphical user interface (GUI) that facilitates enabling a user to control, configure, access, and/or otherwise interact with components of the HLM and/or external components interfaced with the HLM. For example, the GUI may facilitate configuring HLM components, monitoring values from actuators and/or sensors, setting timers and/or reminders, and/or the like. The control assembly 200 may provide visual and/or audible notifications, alarms, and/or the like.

As shown in FIGS. 2A-2B, for example, the illustrative control assembly 200 includes a body 202 having a first portion 204 that is at least approximately rectangular and a second portion 206 that extends away from a front surface 208 of the first portion 204. According to embodiments, the first and second portions 204 and 206 of the body 202 may be integrated, removeably coupled together, permanently coupled together, and/or the like. In embodiments, as shown, the body 202 may include a solid piece, with a control panel insert 210 configured to be disposed within a cavity (not shown) defined in a front surface 212 of the body 202. The control panel insert 210 may include a display device 214 and a number of input control devices 216A, 218A, 220A, and 222A. In embodiments, the display device 214 may be, or include, a touchscreen device configured to receive user input via touch (e.g., by a user's finger, a stylus, and/or the like).

Each of the input control devices 216A, 218A, 220A, and 222A may be configured to be assigned to an actuator on the HLM such as, for example, a small roller pump drive, a large roller pump drive, a centrifugal pump drive, an electronic venous line occluder (EVO), and/or the like. Each of the input control devices 216A, 218A, 220A, and 222A may include a rotatable knob that can be used to adjust an adjustable operating parameter of the corresponding actuator. In embodiments, one or more of the knobs may be configured to be pushed in and/or pulled out to allow further control of additional parameters. In embodiments, one or more of the knobs may be configured to be pushed to toggle through control options, assigned control options by other devices, and/or the like. The control assembly 200 further includes a display region 216B, 218B, 220B, and 222B corresponding to, and disposed adjacent to, each input control device 216A, 218A, 220A, and 222A.

According to embodiments, one or more of the input control device 216A, 218A, 220A, and 222A may be configured to start the corresponding actuator again in the event that the actuator's operation is stopped. For example, the actuator may be a fluid pump actuator (e.g., an arterial blood pump actuator) and may be stopped due to an occurrence of a pump-stop trigger event such as, for example, a detection of a bubble in the line, detection of excessive pressure, and/or the like. That is, for example, the input control device may include a rotatable knob that can be used to directly start the corresponding actuator, without any additional interaction by a user such as, for example, overriding an alarm indication on the display device 214, pressing a global override button on the pump actuator, and/or the like.

According to embodiments, the display region corresponding to an input control device may be configured to display a parameter value associated with the corresponding actuator. That is, in embodiments, for example, each display region 216B, 218B, 220B, and 222B may be displayed above its corresponding input control device 216A, 218A, 220A, and 222A and may be configured to display a value of the parameter adjustable using the input control device 216A, 218A, 220A, and 222A (e.g., a pump speed in revolutions or rotations per minute (rpm), a pump flow rate in liters per minute (lpm), an occlusion value, etc.). In embodiments, the display region may replicate a similar display region that may be found on an ACU associated with the actuator. In embodiments, each input control device 216A, 218A, 220A, and 222A may include a color (e.g., a colored ring) that matches a color affixed to the corresponding actuator. That matching color may be also affixed to a corresponding ACU and/or may be represented in the corresponding display region 216B, 218B, 220B, and 222B.

In embodiments, the control assembly 200 may include any number of input control devices (e.g., 1, 2, 3, 4, 5, 6, etc.) and the number of input control devices may be less than or equal to the number of ACUs in an actuator enclosure (e.g., the enclosure 136 depicted in FIG. 1C). In embodiments, display device 214 and input control devices 216A, 218A, 220A, and 222A may be disposed in the front surface of the body 202 individually, using two different inserts (e.g., an insert for the display device 214 and an insert for the input control devices 216A, 218A, 220A, and 222A), and/or according to any number of other designs. Any number of display devices and/or input control devices may be provided in the body 202 of the control assembly 200.

In embodiments, the body 202 may include more than one piece (e.g., a pair of half-shell pieces configured to be joined together to form the body 202). As shown, the body 202 generally includes a rear surface 224 opposite the front surface 212. In embodiments, as shown, the rear surface 224 may also include a curved portion 226 corresponding to a curved portion 228 of the front surface 212. In embodiments, one or more of the curved portions 226 and 228 may be angled instead of, or in addition to, being curved. A combination of curved aspects and angled aspects may be used. In embodiments, the front surface 212 may include a curved portion 228, while the rear surface 224 is flat (e.g., does not include a curved portion 226). The second portion 206 of the body 202 is formed by at least a curved and/or angled portion 228 of the front surface 212. The second portion 206 may be configured to be used as a hand rest upon which a user may rest, for example, the palm of the user's hand while, and/or between, operating input control devices. The second portion 206 may also facilitate protecting the input control devices from accidental manipulation, damage, and/or the like.

As shown in FIG. 2B, the rear surface 224 may include a mast connection interface 230 configured to facilitate coupling the control assembly 200 to a connection arm 232 configured to connect the control assembly 200 to a mast component 234 via a mast connector 236. As shown, the mast connector 236 may include a moveable, locking connector 236 having a locking device 238 (e.g., a locking wheel, a lever, a hand gear, etc.) for securing the mast connector 236 in place on the mast component 234. In embodiments, when the locking device 238 is loosened, the mast connector may be configured to be slideably moved up and down the mast component 234 and/or rotated around the mast component 234. That is, for example, the mast connector 236 may include an interface cylinder 240 configured to be concentrically disposed around the mast component 234. In embodiments, the mast connector 236 may be oriented in any number of different directions to facilitate connecting to other mast components (e.g., horizontally to facilitate connection to a horizontal mast rail).

The connection arm 232 may be pivotably connected to the mast connection interface 230 such that the control assembly 200 can be at least partially rotated in one or more directions with respect to the connection arm 232. For example, in embodiments, the connection arm 232 may include a ball configured to be coupled to a socket in the mast connection interface 230 to facilitate pivoting the control assembly 200 in any number of different directions. In other embodiments, the connection arm 232 may be connected by a pin to facilitate rotation in one direction.

As is further shown in FIG. 2B, a connection port 242 disposed in the rear surface 224 may be configured to connect a cable 244 to the control assembly 200. In embodiments, the control assembly 200 may be coupled to a peripheral processing unit and/or a bus of the HLM using only one cable 244. That cable 244 may be configured to transport control signals, parameter data, power, and/or the like. The cable 244 may be, include, or be included within, the bus. For example, the bus may be implemented using circuitry within a central system unit, one or more cables configured to couple the central system unit to one or more different components of the HLM. In embodiments, the cable 244 may be configured to be disposed outside of the connection arm 232 and/or mast component 234, while, in other embodiments, the cable 244 (or at least a portion thereof) may be configured to be disposed within at least a portion of the connection arm 232 and/or at least a portion of the mast component 234.

Figure 2C:
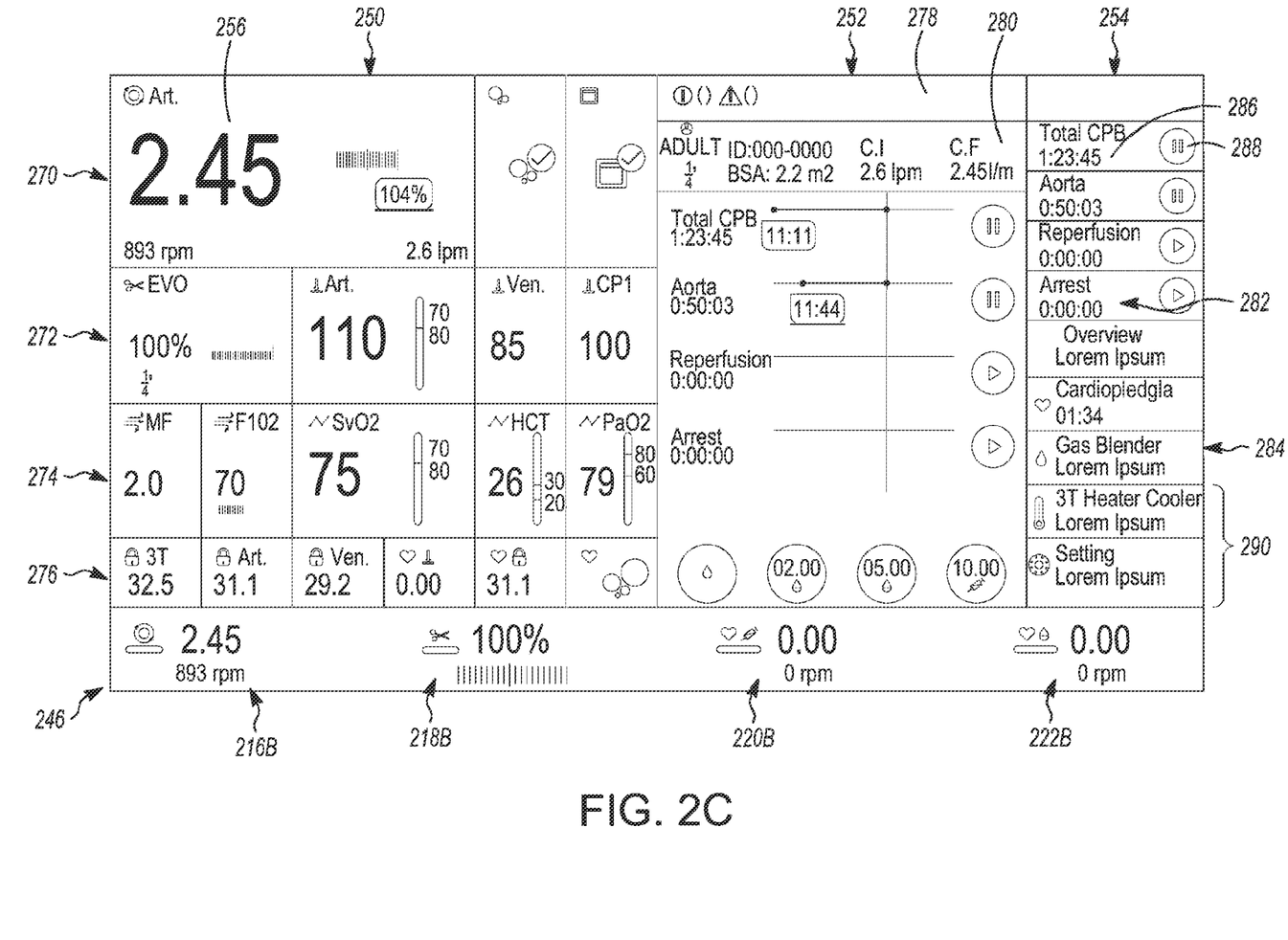
FIG. 2C depicts an illustrative graphical user interface (GUI), in accordance with embodiments of the subject matter disclosed.

According to embodiments, the display device 214 may be configured to present a graphical user interface (GUI) 246, as shown in FIG. 2C. The GUI 246 may include any number of different features and may be configured to facilitate control of one or more HLM components and/or other components, monitoring parameter values, providing notifications and/or alarms, and/or the like. As shown in FIG. 2C, and as mirrored in the conceptual layout 248 depicted in FIG. 2D, the GUI 246 may include a number of presentation areas such as, a monitoring area 250, a dynamic area 252, and a system area 254. According to embodiments, the GUI 246 may include any number of different display areas arranged in accordance with any number of different display schemes. In embodiments, the display areas may be configurable (e.g., selectable, removeable, moveable, etc.), while, in other embodiments, one or more of the display areas may be fixed. That is, for example, in embodiments, the monitoring area 250, the dynamic area 252, and the system area 254 may always be present and may each always occupy the same portion of the GUI 246 so as to facilitate a consistent and predictable user experience, thereby facilitating the efficiency with which a user may utilize the GUI 246.

Figure 2D:
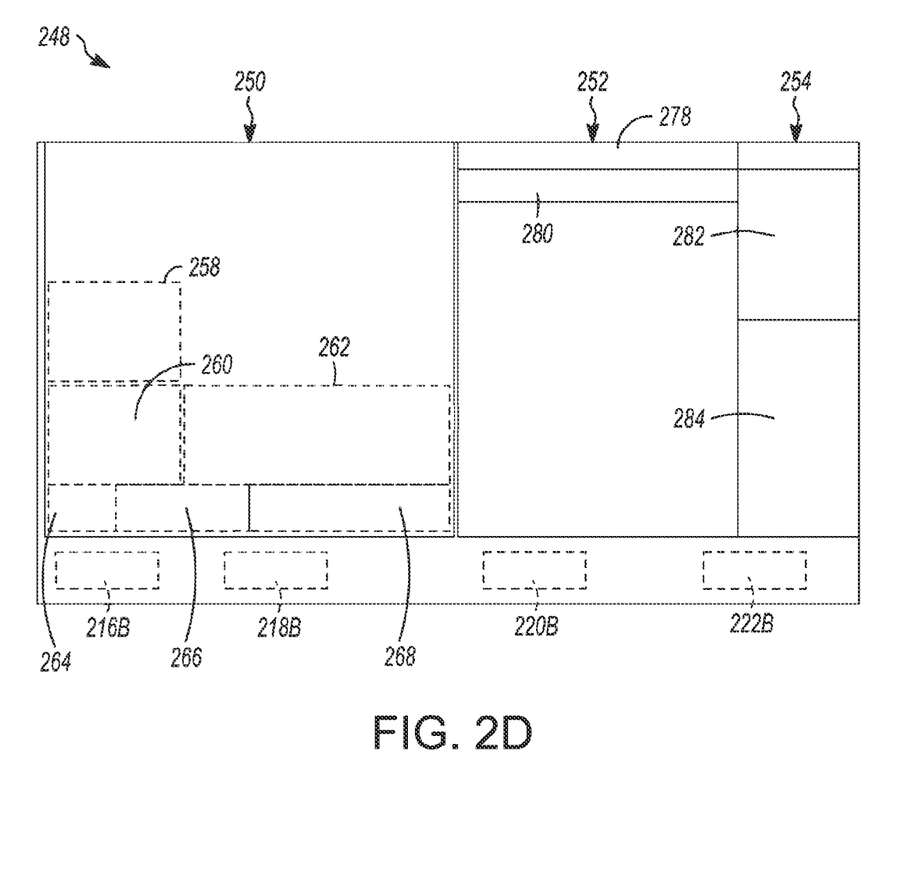
FIG. 2D is a conceptual layout of an illustrative GUI, in accordance with embodiments of the subject matter disclosed.

In embodiments, the monitoring area 250 may be configured to present a number of parameter values obtained from actuators, sensors, and/or other HLM components. According to embodiments, the layout of parameter value display fields may be consistent, while the particular parameters represented may be configurable based on the particular HLM components being used and/or connected in a certain operation. For example, as shown, the monitoring area 250 may include a prominent display field 256 that is configured to present a parameter value corresponding to a parameter of primary interest to a user of the HLM during a particular operation such as, for example, a speed of a pump, or a flow rate, having the most impact on the function of the HLM at that time. The prominent display field 256 may be larger than any other display field in the monitoring area 250 to facilitate its prominence with respect to other aspects of the GUI 246.

As illustrated in FIG. 2D, the monitoring area 250 may further include functional display areas 258, 260, 262, 264, 266, and 268. In embodiments, each of the functional display areas 258, 260, 262, 264, 266, and 268 may correspond to a different function performed by the HLM. For example, in embodiments, the functional display areas 258, 260, 262, 264, 266, and 268 may correspond, respectively, to operation of an electronic venous occlude (EVO), gas blending, blood gas monitoring, temperature monitoring, arterial/venous temperature, and cardioplegia. Each functional display area may include one or more display fields configured to present a parameter value associated with the corresponding function. According to embodiments, the monitoring area 250 may include any number of functional display area and/or display fields contained therein. In embodiments, the existence and/or layout of one or more of the functional display fields may be configurable by a user, pre-determined based on related functions being performed, and/or the like. In embodiments, as shown in FIG. 2C, the monitoring area 250 may be organized into rows dedicated to certain types of data, though the number of display fields in each row may vary. For example, as shown, the first row 270 may include arterial flow data, the second row 272 may include venous flow and/or percent line occlusion and pressure data, the third row 274 may include gas flow and blood gas data (e.g., saturation, partial pressures, etc.), and the fourth row 276 may include temperature data. Rows, display fields, functional display areas, and/or the like may be distinguished using any number of different techniques such as, for example, color-coding, certain types of fonts, images, and/or the like.

In embodiments, the dynamic area 252 may be configured to present interactive display elements configured to facilitate user interaction with the GUI such as, for example, dropdown menus, input fields, virtual buttons, virtual levers, virtual sliders, and/or the like. In embodiments, for example, the dynamic area 252 may present one or more interactive display elements configured to enable a user to input values, set limits, configure alarms, and/or the like. In embodiments, the dynamic area 252 may include a notification bar 278 for displaying notifications, a status bar 280 for displaying data associated with the current procedure/operation, such as the current system configuration, the patient surface area, the needed perfusion flow for the patient, and/or the like. The dynamic area 252 may be configured to present notifications, alarms, indications of unusual situations, and/or the like, such as, for example, by providing pop-up display areas, displaying certain colors, and/or the like.

The system area 254 may be configured to present representations of states of aspects of the HLM system. For example, in embodiments, the system area 254 may present general system information like actual date and time, battery status and general controls, like locking the touch-panel, exit the current procedure or access the setting menu, and/or the like. The system area 254 may further include a timer area 282 and a navigation area 284. The timer area 282 may include any number of different timers, clocks, and/or the like, and may include interactive display elements configured to enable a user to interact with the timers/clocks. For example, the timer area 282 may include a number of timers intended to measure/document the duration of the individual phases of the current procedure/operation, and each timer may include a time display 286 and one or more interactive buttons 288 for starting the timer, stopping the timer, pausing the timer, clearing the timer, and/or the like. The navigation area 284 may include one or more interactive display elements 290 configured to facilitate enabling a user to access different menus, establish display configurations, and/or the like. As shown in FIGS. 2C and 2D, the GUI may further include the display regions 216B, 218B, 220B, and 222B.

The illustrative control assembly 200 and GUI 246 shown in FIGS. 2A-2D are not intended to suggest any limitation as to the scope of use or functionality of embodiments of the present disclosure. The illustrative control assembly 200 and GUI 246 also should not be interpreted as having any dependency or requirement related to any single component or combination of components illustrated therein. For example, in embodiments, the control assembly 200 may include one or more speakers and/or microphones. Additionally, various components depicted in FIGS. 2A-2D may be, in embodiments, integrated with various ones of the other components depicted therein (and/or components not illustrated), all of which are considered to be within the ambit of the present disclosure.

Figure 3:
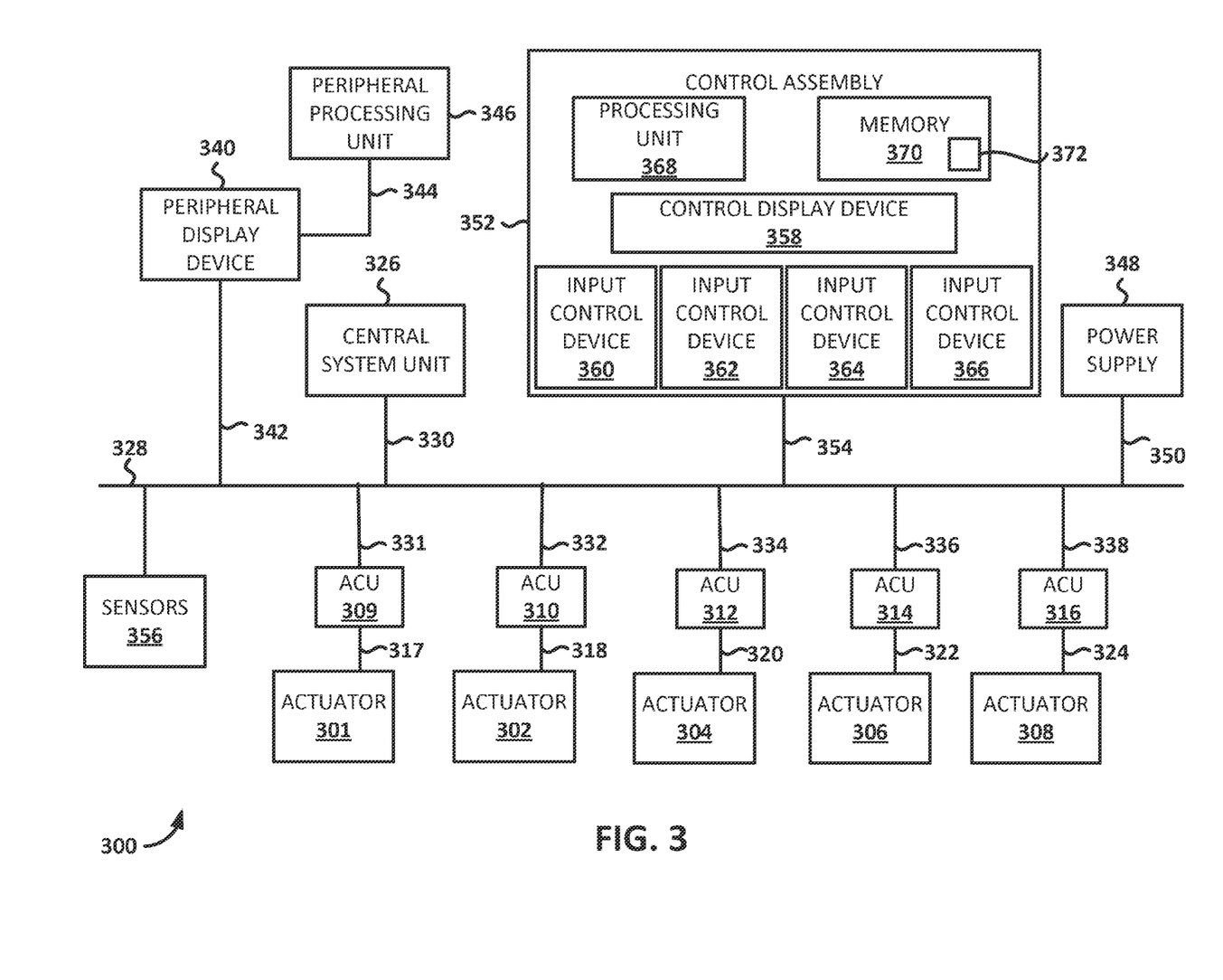
FIG. 3 is a block diagram depicting an illustrative operating environment, in accordance with embodiments of the subject matter disclosed herein.

FIG. 3 is a block diagram depicting an illustrative operating environment 300, in accordance with embodiments of the subject matter disclosed herein. According to embodiments, the illustrative operating environment 300 may be implemented on an HLM or aspects thereof such as, for example, the HLM 100 depicted in FIGS. 1A-1C, the control assembly 200 depicted in FIGS. 2A-2B, and/or the like.

As shown, the operating environment 300 includes a number of actuators 301, 302, 304, 306, and 308. In embodiments, the actuators 301, 302, 304, 306, and 308 may be pump actuators, valve actuators, and/or the like, and may be, be similar to, include, or be included any one or more of the HLM components 116, 118, 120, 122, and 124 depicted in FIGS. 1A-1B. In embodiments, the operating environment 300 includes a number of actuator control units (ACUs) 309, 310, 312, 314, and 316, each of which is operably connected to a corresponding one of the plurality of actuators 301, 302, 304, 306, and 308, respectively, via a communication link 317, 318, 320, 322, and 324, respectively, as shown in FIG. 3. According to embodiments, for example, an ACU may include an adjustable knob and a display configured to display a value of a device parameter adjustable using the knob. The pump ACU may be configured to set and/or adjust a speed or flow rate of the associated pump. Similarly, a line occluder ACU may be configured to set and/or adjust a value of line occlusion, or the free flow corresponding to it.

In embodiments, each of the actuators 301, 302, 304, 306, and 308 may be operably connected to the bus 328 via actuator-bus communication links. In embodiments, as shown in FIG. 3, these connections may not be present. In embodiments, as shown in FIG. 3, each of the ACUs 309 310, 312, 314, and 316 may be configured to be operably connected to the bus 328, via ACU-bus communication links 331, 332, 334, 336, and 338, respectively. That is, for example, while one or more of the actuators 301, 302, 304, 306, and 308 may be functionally coupled to the bus 328, e.g., via the respective ACUs, the actuators 301, 302, 304, 306, and 308 are not directly coupled to the bus 328. In embodiments, for example, one or more of the actuators 301, 302, 304, 306, and 308 may be able to communicate information to the bus 328, but may not be able to be controlled directly via the bus 328. That is, in embodiments, actuators 301, 302, 304, 306, and 308 may be configured to be controlled only through their respective ACUs, and the corresponding input control devices may have communication links only to the ACUs (via the bus), and not directly to the actuators. This arrangement may facilitate, for example, priority of the ACUs over the input control devices.

As is further shown in FIG. 3, the operating environment 300 further includes a peripheral display device 340 configured to present representations of a subset of the set of parameter data received from the actuators 301, 302, 304, 306, and 308, and/or one or more of the ACUs 309, 310, 312, 314, and 316. The peripheral display device 340 may be operably connected, via a communication link 342, to the bus 328. In embodiments, the peripheral display device 340 may additionally, or alternatively, be operably connected, via a communication link 344, to a peripheral processing unit 346, where the peripheral processing unit 346 may be configured to operate the peripheral display device 340, save data inputted to the peripheral display device, and/or the like. The operating environment 300 includes a power supply 348 operably connected to the bus 328 via a communication link 350.

In embodiments, the peripheral processing unit 346 may be implemented as an interface device configured to facilitate operably (or at least communicably) coupling peripheral devices to the HLM such as, for example, the peripheral display device 340, third party medical devices (e.g., pulse oximeters, capnographs, ventilators, etc.), lighting devices, imaging devices, gas blenders, heaters, coolers, and/or the like.

A control assembly 352 is operably connected to the bus 328 via a control communication link 354. In embodiments, the communication link 354 may include a single cable configured to transport control signals, parameter data (e.g., from one or more sensors 356), power, and/or the like. In embodiments, sensors 356 may include, for example, bubble sensors, pressure sensors, flow sensors, level sensors, temperature sensors, blood gas sensors, and/or the like. In embodiments, the control assembly 352 includes a control display device 358 and a plurality of input control devices 360, 362, 364, and 366. In embodiments, the control assembly 352 may include any number of input control devices (e.g., 1, 2, 3, 4, 5, 6, etc.) and the number of input control devices may be less than or equal to the number of ACUs in an actuator enclosure (e.g., the enclosure 136 depicted in FIG. 1C). In embodiments, each of the input control devices 360, 362, 364, and 366 may be operably connected to the bus 328 via the communication link 354. According to embodiments, any number of the various components of the operating environment 300 may have associated therewith a unique identifier. For example, one component may communicate with another component by associating the other component identifier with the communication intended therefor. In this manner, communications between any two or more components of the operating environment may be placed on the bus 328 and recognized by the intended recipient based on the identifier of the intended recipient.

According to embodiments, the control display device 358 may be configured to display representations of a subset of the set of parameter data received. For example, the control display device 358 may be configured to display a first subset of the set of parameter data, while the peripheral display device 340 may be configured to display a second subset of the set of parameter data, where the first and second subsets may not be equal. In this manner, for example, embodiments of the control display device 358 may be configured to present only specified parameters to the user such as, for example, all of the important parameters for a certain procedure, while parameters of somewhat less importance may be presented by the peripheral display device 340.

In embodiments, the control assembly 352 may include a processing unit 368 and a memory 370. The processing unit 370 may, for example, be configured to control the control display device by, for example, providing the parameters to display, providing the defining a layout of display elements, process user input, and/or the like. The processing unit 368 may include, for example, one or more processors configured to execute computer-executable instructions 372 stored in the memory 370 to cause the processing unit 368 to perform one or more functions such as, for example, to assign one or more of the input control devices 360, 362, 364, and 366 to one or more actuators 302, 304, 306, and 308, one or more ACUs 310, 312, 314, and 316, and/or the like. Note that, in embodiments, one or more ACUs 309 and/or actuators 301 may not be operably connected to an input control device 360, 362, 364, and 366.

In embodiments, each of the input control devices 360, 362, 364, and 366 may be assignable to one or more other components of the operating environment 300 that can be configured to be controlled by an input control device. In embodiments, each of the communication links between the input control devices and the respective actuators, via the corresponding ACUs, may be optional with respect to a respective communication link between the actuator and its corresponding ACU such that each of the input control devices is capable of controlling its corresponding actuator via the corresponding ACU (but having no priority over the ACU—that is, e.g., the ACU prevails over the input control device such that an input entered directly at the ACU may override a command entered at the input control device). In embodiments, each of the input control devices 360, 362, 364, and 366 is operably connected to a corresponding ACU, but is not configured to prevail over the corresponding ACU. In embodiments, one or more of the ACUs may be regarded as emergency ACUs (e.g., those ACUs 138, 140, 142, and 144 that are disposed in the enclosure 136 depicted in FIG. 1C).

In embodiments, for example, the actuator 302 may be controlled by its respective ACU 310 in two ways—either via the communication link 318 or via the respective input control device 360. In embodiments, the ACU 310 may have priority over the input control device 360 in case, for instance, of bus 328 failure, as the actuator 302 can always be controlled by the ACU 310 via communication link 318, but, in that instance, can no longer be controlled by the input control device 360. According to embodiments, as the philosophy of the HLM is to use the ACUs placed in the lower enclosure primarily for emergencies and not for normal operation, the lower ACUs may have priority over the input control devices because they still can control actuators in case the input control devices cannot. In embodiments, in normal operation, causing an input to either an input control device or an ACU may provide the same result on the actuator.

Any one or more of the communication links described herein may be, or include, a wired link, a wireless communication link such as, for example, a short-range radio link, such as Bluetooth, IEEE 802.11, a proprietary protocol, a combination of wired and wireless links, and/or the like. The term "communication link" may refer to a mechanism for communicate some type of information (e.g., control signals, parameter data, etc.) and/or energy (e.g., electrical power) in at least one direction between at least two locations, and should not be understood to be limited to a direct, persistent, or otherwise limited communication channel. That is, according to embodiments, a communication link may be a persistent communication link, an intermittent communication link, an ad-hoc communication link, and/or the like. A communication link may refer to direct communications between components and/or indirect communications that travel between components via at least one other device (e.g., a repeater, router, hub, and/or the like). A communication link may facilitate uni-directional and/or bi-directional communication between components. For example, in embodiments, one or more input control devices 360, 362, 364, and 366 may be configured to communicate, via a wired and/or wireless link, with corresponding ACUs 310, 312, 314, and 316.

In embodiments, a combination of an actuator, a corresponding ACU, and a corresponding input device may be referred to herein as a blood pump system. According to embodiments, one or more of the input control devices 360, 362, 364, and 366 may include a rotatable knob operably connected to a pump actuator, and the corresponding ACU may configured to determine that the pump actuator has been stopped in response to a pump-stop trigger event; determine that the rotatable knob has been rotated to a first position; and in response to determining that the rotatable knob has been rotated to the first position, start the pump actuator. In this manner, the ACU may be configured to start the corresponding pump actuator without any interaction, by a user, with the display device. In embodiments, the first position may, for example, correspond to an initial activation condition with zero flow, and the ACU may be further configured to determine that the rotatable knob has been rotated to a second position, where the second position corresponds to a positive flow speed; and cause, in response to determining that the rotatable knob has been rotated to the second position, the pump actuator to operate at the positive flow speed.

In embodiments, the control assembly processing unit 368 may be configured to display, in response to the ACU detecting the occurrence of the pump-stop trigger event, an alarm notification; and continue to display the alarm notification while the ACU causes the pump actuator to start. In embodiments, the control assembly processing unit 368 may be configured to determine that the pump-stop trigger event has been resolved; and clear the alarm notification in response to determining that the pump-stop trigger event has been resolved. That is, in embodiments, the control assembly processing unit 368 may be configured to manage alarm situations independently of the starting of the pump by via interaction solely with the input control device.

According to embodiments, any one or more of the components of the illustrative operating environment 300 may be implemented on one or more computing devices. A computing device may include any type of computing device suitable for implementing aspects of embodiments of the disclosed subject matter. Examples of computing devices include specialized computing devices or general-purpose computing devices such "control units," "control assemblies," "workstations," "servers," "hand-held devices," "heart lung machines," "controllers," and the like, all of which are contemplated within the scope of FIG. 3, with reference to various components of the operating environment 300.

In embodiments, a computing device includes a bus that, directly and/or indirectly, couples the following devices: a processing unit, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wired and/or wireless device, a keyboard, a pen, a voice input device, a touch input device, a touchscreen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally, any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The illustrative operating environment 300 shown in FIG. 3 is not intended to suggest any limitation as to the scope of use or functionality of embodiments of the present disclosure. The illustrative operating environment 300 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
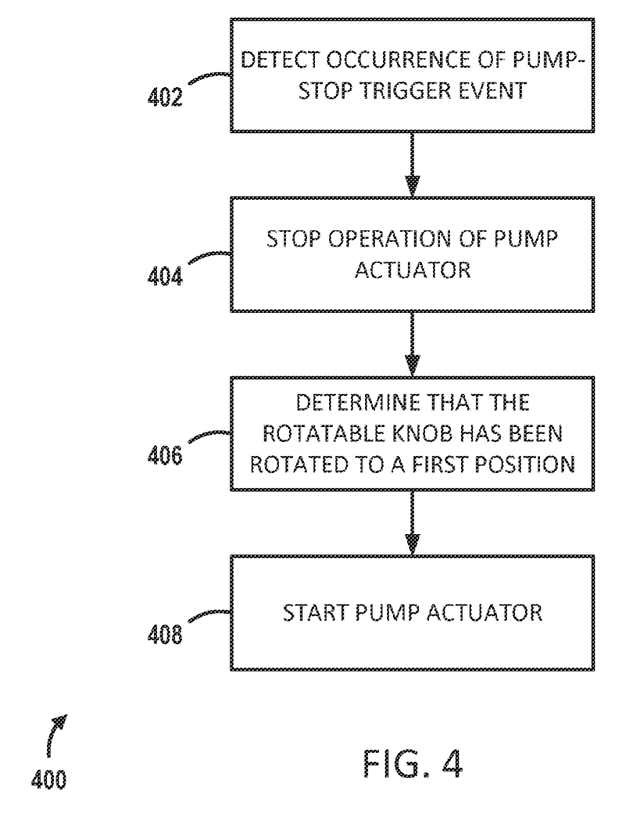
FIG. 4 is a flow diagram depicting an illustrative method of operating a heart lung machine (HLM), in accordance with embodiments of the subject matter disclosed herein.

FIG. 4 is a flow diagram of an illustrative method 400 of operating a heart lung machine (HLM). According to embodiments, the HLM may be, or be similar to, the HLM 100 depicted in FIGS. 1A-1C, and may include, for example, a pump actuator, an actuator control unit (ACU) operably connected to the pump actuator, a processing unit configured to receive a set of parameter data from the actuator, a display device configured to present a subset of the parameter data, and an input control device operably connected to the pump actuator. The pump actuator may correspond to a fluid pump such as, for example, an arterial pump. The input control device includes a rotatable knob.

According to embodiments, the method 400 may include detecting an occurrence of a pump-stop trigger event (block 402); stopping operation of the pump actuator (block 404); determining that the rotatable knob has been rotated to a first position (block 406); and starting the pump actuator in response to determining that the rotatable knob has been rotated to the first position (block 408). In embodiments, the first position may correspond, for example, to an initial activation condition with zero flow and, accordingly, the method 400 may further include determining that the rotatable knob has been rotated to a second position, where the second position correspond to a positive flow speed; and causing the pump actuator to operate at the positive flow speed in response to determining that the rotatable knob has been rotated to the second position.

According to embodiments, the method 400 includes starting the pump actuator in response to determining that the rotatable knob has been rotated to the first position without receiving any indications of interaction, by a user, with the display device. That is, for example, according to embodiments, the restarting of the pump after a pump stop (e.g., that occurred in response to a pump-stop trigger event such as an error condition) can be achieved by only interaction with the rotatable knob. This arrangement may facilitate more efficient operation than prior art pump systems that, for example, require a user to override an alarm by pressing a button on a display, pressing a global override button, or the like, as the starting, stopping, and speed adjustment of the pump can all be controlled by the rotatable knob, such that the user need not remove his hand from the knob to perform any of these actions. That is, for example, the method 400 may include starting the pump actuator in response to determining that the rotatable knob has been rotated to the first position without receiving any indications of interaction, by a user, with a global override button. In embodiments, a display device may be configured to display, in response to detecting the occurrence of the pump-stop trigger event, an alarm notification; and to continue to display the alarm notification while the user is starting the pump actuator via the rotatable knob. Embodiments of the method 400 may further include automated and/or manual processes for determining that the pump-stop trigger event has been resolved; and clearing the alarm notification in response to determining that the pump-stop trigger event has been resolved.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A heart lung machine (HLM), comprising:
a fluid pump;
a pump actuator configured to control the fluid pump;
an actuator control unit (ACU) operably connected to the pump actuator;
a processing unit configured to receive a signal from the pump actuator;
an input control device operably connected to the pump actuator, the input control device comprising a rotatable knob, wherein the ACU is configured to:
determine that the pump actuator has been stopped in response to a pump-stop trigger event;
thereafter, determine that the rotatable knob has been rotated to a first position after the pump actuator has been stopped; and
thereafter, restart the pump actuator solely upon determining that the rotatable knob has been rotated to the first position.

2. The HLM of claim 1, wherein the first position corresponds to an initial activation condition with zero flow.

3. The HLM of claim 1, wherein the ACU is further configured to:
after restarting the pump actuator, determine that the rotatable knob has been rotated to a second position, wherein the second position corresponds to a positive flow speed; and
cause the pump actuator to run the fluid pump at the positive flow speed.

4. The HLM of claim 1, wherein the processing unit is configured to display an alarm notification that the ACU has detected a pump-stop trigger event on a display of the HLM.

5. The HLM of claim 4, wherein the processing unit is configured to clear the alarm notification upon restarting the pump actuator.

6. The HLM of claim 1, wherein the fluid pump is an arterial pump.

7. The HLM of claim 1, wherein the input control device acts in parallel to the ACU.

8. The HLM of claim 1, wherein the ACU is located in an enclosure of a lower housing of a trolley of the HLM.

9. The HLM of claim 8, wherein the fluid pump and the pump actuator are mounted on the trolley.

10. A heart lung machine (HLM) comprising:
a plurality of actuators;
a peripheral processing unit configured to receive a set of parameter data from the plurality of actuators;
a peripheral display device configured to present a subset of the set of parameter data;
a plurality of actuator control units (ACUs), each of the plurality of ACUs operably connected to one of the plurality of actuators;
a control assembly comprising a control display device and a plurality of input control knobs, wherein each of the control input knobs is operably connected to one of the plurality of actuators; and
a trolley comprising a base and a mast assembly coupled to the base and extending upwards from the base;
wherein the peripheral display device is separate from the control assembly;
wherein the control assembly, including the control display device, is coupled to the mast assembly at a first location;
wherein the peripheral display device is coupled to the mast assembly at a second location spaced apart from the control assembly and the control display device;
wherein each ACU is configured to:
determine that its associated actuator has been stopped in response to a stop trigger event;
thereafter, determine that its associated input control knob has been rotated to a first position after the actuator has been stopped; and
thereafter, restart the actuator solely upon determining that the rotatable knob has been rotated to the first position.

11. The HLM of claim 10, wherein the first position corresponds to an initial activation condition with zero flow.

12. The HLM of claim 10, wherein each ACU is further configured to:
after restarting its associated actuator, determine that its associated rotatable knob has been rotated to a second position, wherein the second position corresponds to a positive flow speed; and
cause the associated actuator to run a fluid pump at the positive flow speed.

13. The HLM of claim 10, wherein the control display device is configured to display an alarm notification that one of the plurality of ACUs has detected a pump-stop trigger event.

14. The HLM of claim 10, wherein the plurality of ACUs are located in an enclosure in the base of the trolley of the HLM.

15. The HLM of claim 14, wherein the enclosure is a drawer.

16. The HLM of claim 14, wherein the enclosure is a cabinet.

\* \* \* \* \*